| United States Patent [19] | [11] | 4,111,971 |
|---|---|---|
| Sellmann et al. | [45] | Sep. 5, 1978 |

[54] PROCESS FOR THE MANUFACTURE OF METAL-AZOMETHINE COMPLEX COMPOUNDS

[75] Inventors: Dieter Sellmann, Paderborn; Ernst Thallmair, Baierbrunn, both of Fed. Rep. of Germany

[73] Assignee: Hoechst Aktiengesellschaft, Frankfort am Main, Fed. Rep. of Germany

[21] Appl. No.: 736,080

[22] Filed: Oct. 27, 1976

[30] Foreign Application Priority Data

Oct. 29, 1975 [DE] Fed. Rep. of Germany ....... 2548330

[51] Int. Cl.$^2$ .................. C07F 11/00; C07F 9/00; C07F 13/00; C07F 15/00

[52] U.S. Cl. .................. 260/438.5 R; 252/431 N; 260/429 C; 260/439 R; 260/668 R; 260/673; 260/673.5; 260/677 R

[58] Field of Search .................. 260/429 C, 438.5 R, 260/439 R, 429 R

[56] References Cited

PUBLICATIONS

Candlin et al., Reactions of Transition-Metal Complexes, Elsevier Publ. Co., N. Y., pp. 83 to 85, 88 and 89 (1968).
Cotton, Progress in Inorganic Chemistry, Interscience Publ., N. Y., Vol. 7, pp. 103, 104 and 195 to 201 (1966).
Knaub et al., Ber. 103, 3744 (1970).
Chem. Rev., 63, pp. 490, 491, 492, 495 (1963).
Fischer et al., Ber. 103, 1262–1263 (1970).
Vogler, J.A.C.S., Vol. 90, pp. 5943–5945 (1968).

*Primary Examiner*—Helen M. S. Sneed
*Attorney, Agent, or Firm*—Curtis, Morris & Safford

[57] ABSTRACT

Metal-azomethine complex compounds are prepared by condensing metal-ammonia complex compounds with organic carbonyl compounds. The azomethine complexes obtained constitute suitable catalysts for various reactions.

13 Claims, No Drawings

PROCESS FOR THE MANUFACTURE OF METAL-AZOMETHINE COMPLEX COMPOUNDS

This invention relates to a process for the manufacture of azomethine-metal complex compounds by condensation of metal-ammonia complex compounds with organic carbonyl compounds.

Metal complex compounds carrying azomethines as ligands are of interest as they can be used for examining the behaviour of azomethines which are unstable in the free state. For example, the azomethine deriving from acetone and ammonia is only known as a polymer. Therefore, many attempts have been made to prepare metal complex compounds carrying azomethines as ligands.

It has been proposed to use ketimines as starting compounds. But this process is limited, of course, to such ketimines as can be isolated in substance. Thus, the most interesting aliphatic azomethines cannot be prepared in this manner. It is also possible to synthetize ketimine-carbonyl-metal-complex compounds by reacting metal complexes containing as ligands carbenes besides carbonyl groups with oximes of ketones. The carbene complexes to be used are, however, difficultly accessible and, moreover, by this method the ketimine complexes can be obtained in a very poor yield only.

The present invention provides a process for the manufacture of metal-azomethine complex compounds by reacting metal-ammonia complexes with organic carbonyl compounds of the formula R—CO—R' in which R represents an aromatic radical, preferably the phenyl radical, or an aliphatic radical, preferably an alkyl radical having from 1 to 15 carbon atoms, preferably 1 to 3 carbon atoms, R' represents — independent of R— an aryl radical, preferably a phenyl radical, or an aliphatic radical, especially an alkyl radical having from 1 to 15 carbon atoms, preferably 1 to 3 carbon atoms, or R' represents hydrogen, or the formula R—CO—R' is an aliphatic cyclic ketone preferably having 5 to 7 and especially 6 carbon atoms.

The metal-ammonia complex compounds to be used have as central atom the atom of an element of a subgroup, preferably of subgroups V to VIII and more preferably of subgroup VI of the periodic table.

The metal-ammonia complex can carry from 1 to 6 ammonia ligands for each central atom, preferably from 1 to 3 and more preferably 1 ligand per central atom. Besides ammonia the metal-ammonia complex compounds may carry further ligands, which are, however, immaterial to the process of the invention. It proved especially advantageous to have carbonyl compounds as further ligands.

The metal-ammonia complex compounds can be present as cation, as anion or as neutral molecule. The use of uncharged ammonia complexes proved to be especially advantageous.

Suitable metal-ammonia complexes are, for example, $(OC)_5CrNH_3$, $(OC)_5MoNH_3$ or $(OC)_5WNH_3$.

To carry out the reaction in the most simple case the metal-ammonia complex is dissolved in the respective carbonyl component and the solution is allowed to stand for a while. According to the preferred embodiment of the reaction the carbonyl compound and the metal-ammonia complex are heated to 30°–90° C, in general for 2 to 20 hours, in the presence of a water-absorbing agent until the reaction is complete. In many cases the addition of a small amount of a base, for example potassium methanolate proved to be of advantage.

The process proceeds according to the following reaction equation:

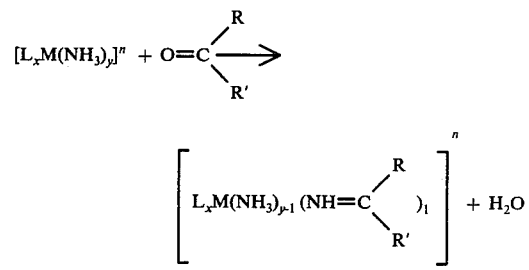

in which
 n stands for an integer of from −3 to +3, preferably zero,
 L represents identical or different ligands,
 M is a central atom (of an element of a sub group),
 y means an integer of from +1 to +6, preferably +1 to +3, more preferably +1, and
 x means an integer of from zero to +5 with 4 being less than or equal to (x+y) which is less than or equal to 6.

It results from the above equation that a charge of the metal complex remains unchanged during the reaction. Furthermore, water is formed in the reaction.

It proved particularly advantageous to remove the generated water from the reaction mixture during the reaction.

The carbonyl compounds can be used as reaction medium either undiluted or in admixture with solvents which are inert under the reaction conditions. Suitable solvents are especially polar as well as non-polar organic solvents such as methanol, tetrahydrofurane, dioxane, petroleum, ether, benzene, or toluene. When toluene is used the water formed can be distilled off in the form of an azeotrope.

The reaction in solution is carried out at a temperature of from 20° to 150° C, preferably 50° to 100° C. The reaction can be performed with equimolar amounts of the carbonyl component and ammonia complex, but to improve the yield an excess of the carbonyl component is desirable. It is advantageous to maintain a molar proportion of carbonyl component to ammonia complex of from 1:1 to 1,000 to 1, preferably 50:1 to 500:1.

In general, the metal-ammonia complexes to be used according to the invention are readily accessible. For example, ammonia complexes of the general formula $(CO)_5MNH_3$ can be easily prepared from the corresponding hexacarbonyl-metal compounds of the formula $M(CO)_6$ and ammonia. Hence, the process of the invention permits in simple manner the synthesis of azomethine complex compounds from starting compounds that are easy to obtain and in a good yield.

When volatile metal-ammonia complexes are used the process can also be carried out in the gaseous phase. Difficultly volatile metal-ammonia complex compounds react also when a current of the gaseous carbonyl compound is passed thereover at elevated temperature.

The metal-azomethine complex compounds obtained by the process of the invention can be used in many fields. They are suitable, for example, as catalysts for the oligomerization of acetylene with formation of benzene and cyclooctatetraene. Especially good results in this respect are obtained with the corresponding, nickel, cobalt, iron and chromium compounds. Compounds of the formula $(CO)_5M^{VI}(NH=CRR')$, i.e. compounds which still contain carbonyl groups and are derived from elements of subgroup VI, are expecially suitable for the trimerizatin of diphenylacetylene with formation of hexaphenyl benzene.

Azomethine complex compounds containing as central atom an element of subgroup VIII and carbonyl groups as ligands can be used as catalysts for the reaction of carbon monoxide with olefins or alcohols with formation of carboxylic acids.

The following examples illustrate the invention.

EXAMPLE 1

1.00 g of $(OC)_5CrNH_3$ (4.8 mmols) in 30 ml of acetone and 15 mg of $KOCH_3$ and 2 g of $MgSO_4$ were heated to boil for 4 hours, the reaction mixture was filtered and evaporated to dryness whereby the compound $(OC)_5Cr-NH=C(CH_3)_2$ remained behind as a yellow oil. After purification, preferably by chromatography in pentane/toluene (1:1 mixture) at $-20°$ C over $SiO_2$, 0.89 g of crystalline $(OC)_5Cr-NH=C(CH_3)_2$, i.e. 75% of the theory, calculated on $(OC)_5CrNH_3$, was obtained.

EXAMPLE 2

1.00 g of $(OC)_5CrNH_3$ (4.8 mmols) in 30 ml of cyclohexanone, 15 mg of $KOCH_3$ and 2 g of molecular sieve (4 A) were heated for 5 hours to 55° C. Next, the reaction mixture was filtered and evaporated to dryness whereby $(OC)_5Cr-NH=C_6H_{10}$ remained behind as solid matter. After purification, preferably by chromatography in toluene at $-20°$ C over $SiO_2$, 1.09 g of crystalline $(OC)_5Cr-NH=C_6H_{10}$, corresponding to 78% of the theory, calculated on $(OC)_5CrNH_3$, were obtained.

What is claimed is:

1. A process for the manufacture of azomethine metal complex compounds having the formula

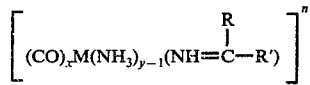

in which $n$ is an integer of from $-3$ to $+3$

M is an element of subgroups V to VIII of the periodic table $y$ is the integer 1

$x$ is an integer of from 0 to $+5$ and 4 is less than or equal to $(x+y)$ which is less than or equal to 6

R is an aromatic radical or an alkyl radical having from 1 to 15 carbon atoms

R' is an aromatic radical or an alkyl radical having from 1 to 15 carbon atoms or hydrogen, which comprises condensing a metal ammonia complex of the formula

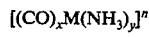

with a carbonyl compound of the formula R—CO—R' where R and R' are as defined above or where the group R—CO—R' is an aliphatic cyclic ketone having 5 to 7 carbon atoms.

2. The process of claim 1, wherein R and R' represent alkyl radicals having from 1 to 3 carbon atoms.

3. The process of claim 1, wherein the carbonyl component is an aldehyde of the formula R—CHO in which R represents an aromatic radical or an alkyl radical having from 1 to 15 carbon atoms.

4. The process of claim 3, wherein the carbonyl compound is acetone.

5. The process of claim 1, wherein $m$ is an element of subgroup VI of the periodic table.

6. The process of claim 1, wherein $y$ is an integer in the range of from 1 to 3.

7. The process of claim 1, wherein $n$ is zero.

8. The process of claim 1, wherein the condensation is carried out in the presence of polar or non-polar organic solvents.

9. The process of claim 1, wherein the metal-ammonia complex compound is reacted in the solid phase with the gaseous carbonyl compound.

10. The process of claim 1, wherein the metal-ammonia complex compound and the carbonyl compound are reacted with one another in the gaseous phase.

11. The process of claim 8, wherein the condensation is carried out at a temperature of from $+20°$ to $+150°$ C.

12. The process of claim 1, wherein the carbonyl compound, R—CO—R' is an aliphatic cyclic ketone having 5 to 7 carbon atoms.

13. The process of claim 12, wherein R—CO—R' is an aliphatic cyclic ketone having 6 carbon atoms.

* * * * *